United States Patent [19]

Sakamoto et al.

[11] Patent Number: 4,925,445
[45] Date of Patent: May 15, 1990

[54] GUIDE WIRE FOR CATHETER

[75] Inventors: Hidetoshi Sakamoto, Fujinomiya; Kenjiro Uematsu, Numazu; Masashi Momota, Fujinomiya; Susumu Tanabe, Sagamihara; Tatsuo Suzuki, Yokohama; Toshihiko Endo, Fuji, all of Japan

[73] Assignee: Fuji Terumo Co., Ltd., Fujinomiya, Japan

[21] Appl. No.: 309,029

[22] Filed: Feb. 9, 1989

Related U.S. Application Data

[63] Continuation of Ser. No. 777,003, Sep. 17, 1985, abandoned, which is a continuation-in-part of Ser. No. 542,373, Oct. 14, 1983, abandoned.

[30] Foreign Application Priority Data

Sep. 16, 1983 [JP] Japan ............... 58-169467
Sep. 16, 1983 [JP] Japan ............... 58-169468

[51] Int. Cl.$^5$ ................................. A61M 37/00
[52] U.S. Cl. ..................... 604/95; 604/281; 128/772
[58] Field of Search .............. 604/280–284, 604/93–95, 164, 170; 128/656–658, 772, 207.14

[56] References Cited

U.S. PATENT DOCUMENTS

| | | | |
|---|---|---|---|
| 3,416,531 | 12/1968 | Edwards | 604/95 |
| 3,528,406 | 9/1970 | Jeckel | 604/95 |
| 3,547,103 | 12/1970 | Cook | 128/772 |
| 3,558,369 | 1/1971 | Wang et al. | 148/11.5 |
| 3,605,725 | 9/1971 | Bentov | 604/280 |
| 3,620,212 | 11/1971 | Fannon, Jr. | 128/130 |
| 3,789,841 | 2/1974 | Antoshkiw | 128/772 |
| 3,890,977 | 6/1975 | Wilson | 604/281 |
| 4,037,324 | 7/1977 | Andreasen | 32/14 A |
| 4,233,690 | 11/1980 | Akins | 623/2 |
| 4,283,233 | 8/1981 | Goldstein et al. | 148/11.5 R |
| 4,411,655 | 10/1983 | Schreck | 604/104 |
| 4,425,908 | 1/1984 | Simon | 128/1 R |
| 4,427,000 | 1/1984 | Ueda | 128/6 |
| 4,503,569 | 3/1985 | Dotter | 128/343 |
| 4,512,338 | 4/1985 | Balko et al. | 128/1 R |
| 4,580,568 | 4/1986 | Gianturco | 128/345 |
| 4,601,283 | 7/1986 | Chikama | 128/4 |
| 4,665,906 | 5/1987 | Gervis | 128/92 R |

OTHER PUBLICATIONS

Cordis Corporation, *Cordis Ducor® and the Angiographic System*, pp. 2–16, 1973.

"Shape Memory and Super-elasticity Effects in NiTi Alloys", Yuichi Suzuki, pp. 185–192.

Nihon Kinzoku Gakkai Kaiho (The Report of the Japan Institute of Metals), vol. 22, No. 1 (1983), pp. 33–41, and FIG. 2.

*Primary Examiner*—C. Fred Rosenbaum
*Assistant Examiner*—Sharon Rose
*Attorney, Agent, or Firm*—Frishauf, Holtz, Goodman & Woodward

[57] ABSTRACT

A guide wire for a catheter having a body portion comparatively high in rigidity and a distal end portion comparatively flexible.

At least portions of the body portion and the distal end portion are formed of a super-elastic metallic member. At least portions of inner core portions on the body portion's side and on the distal end portion's side, both of which are coated by a plastic, are formed of the super-elastic metallic member, and at least a portion of the inner core portion on the distal end portion's side is made smaller in cross-section than the inner core portion on the body portion's side.

In consequence, the catheter can be reliably and readily introduced to a predetermined position.

12 Claims, 6 Drawing Sheets

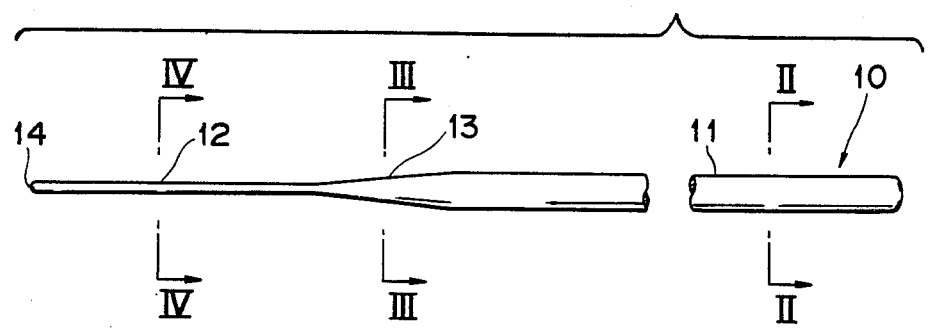
FIG. 1
FIG. 2　　FIG. 3　　FIG. 4
  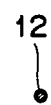
FIG. 5A　　　　　　FIG. 5B
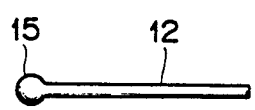 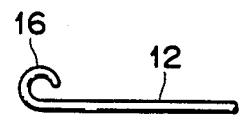
FIG. 5C　　　　　　FIG. 5D
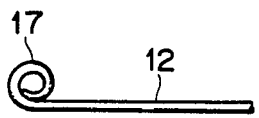 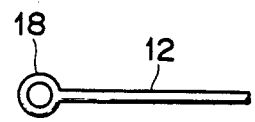

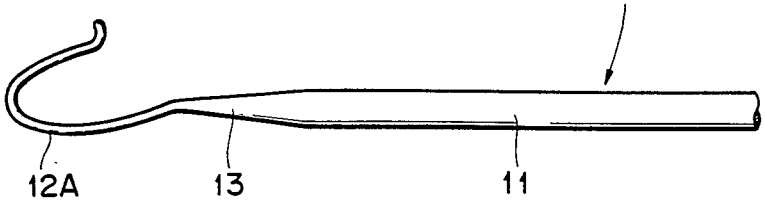
FIG. 6A
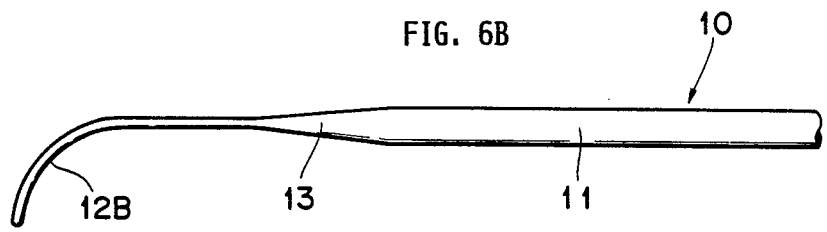
FIG. 6B
FIG. 7
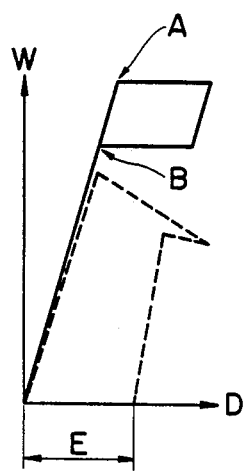
FIG. 8
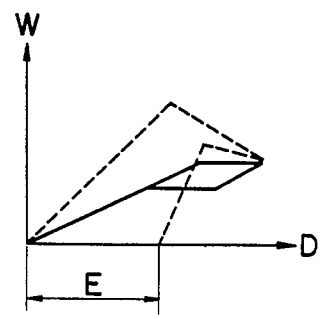

FIG. 11   FIG. 12   FIG. 13
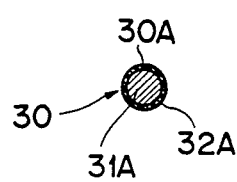
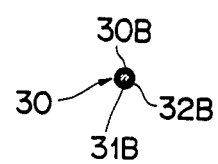
FIG. 14A   FIG. 14B
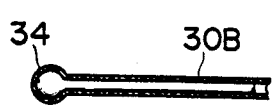
FIG. 15A
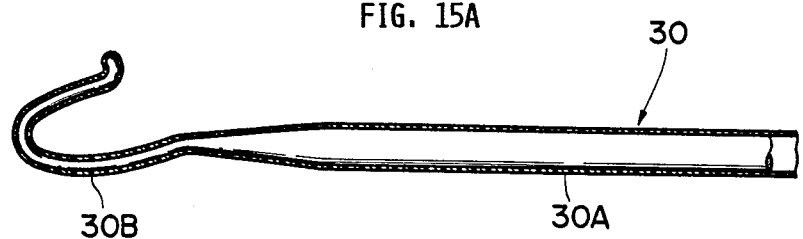
FIG. 15B
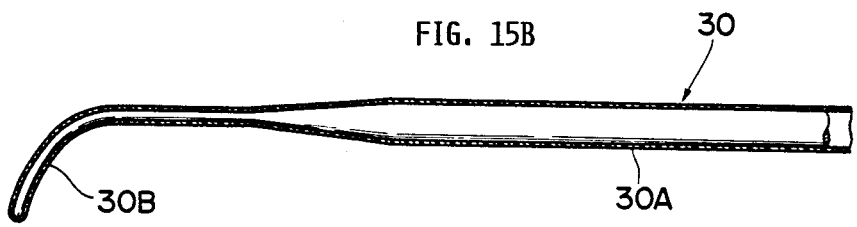

GUIDE WIRE FOR CATHETER

This application is a continuation, of application Ser. No. 06/777,003, filed Sept. 17, 1985, now abandoned which is a CIP of Ser. No. 06/542,373 filed Oct. 14, 1983 (abandoned).

BACKGROUND OF THE INVENTION

1. FIELD OF INVENTION

This invention relates to a guide wire for a catheter for making the catheter guidable, and more paticularly to a guide wire for a catheter for making the catheter for the medical treatment or tests introducible to a predetermined position in a blood vessel, digestive duct, trachea, other body cavities or the like and retainable thereat.

2. DESCRIPTION OF THE PRIOR ART

Heretofore, as a guide wire for a catheter, there has been used a coil-shaped guide wire formed of a stainless steel wire, a piano wire or a monofilament-shaped guide wire made of plastics. Each of the above-mentioned guide wires of the prior art incorporates a general metallic material such as a stainless steel wire or piano wire progressively being reduced in sectional area from a body portion to a distal end portion thereof in a portion or over the total length of its interior, whereby the guide wire is formed of the body portion comparatively high in rigidity and the distal end portion comparatively flexible.

As typified in the case of retaining the Angiographic Catheter at a predetermined position in a blood vessel, in many cases, the aforesaid guide wire is percutaneously inserted into the blood vessel by use of an introducing needle, the distal tip opening portion of the catheter is covered onto a proximal end portion of the guide wire disposed outside of a human body, and the catheter is inserted into the blood vessel with the guide wire being utilized as an arbor. Therefore, a certain level of rigidity is given to the body portion of the aforesaid catheter so that the guide wire is made smoothly insertable into the blood vessel against a resistance generated between the outer surface of the guide wire and the tissues of the human body and the catheter is made guidable against a resistance generated between the outer surface of the guide wire and the inner surface of the catheter.

However, as described above, since the body portion of the conventional guide wire is made of the general metallic material and plastic deformation is caused to the body portion when a certain value of displacement is exceeded, the guide wire may be buckled depending on the skill in manual operation, whereby the buckled portion may be turned into an unrestorable deformed portion, and this deformed portion forms a considerable obstruction against the advance of the catheter, so that difficulties are felt for an operation of smoothly introducing the catheter. Furthermore, in the case of guiding the catheter by previously curving the distal end portion of the catheter so that the catheter can be readily inserted into the predetermined position in the blood vessel, the catheter is covered onto the guide wire and comes into the state of being straightened. Hence, the resistance of the catheter covered onto the guide wire is increased, whereby a possibility of occurrence of a trouble caused by the aforesaid buckling is increased.

In order to have the catheter reach the predetermined position of the blood vessel after the catheter together with the guide wire has been inserted into the blood vessel, it is necessary to further advance in the blood vessel the distal end portion of the guide wire projected a predetermined length from the distal end opening of the catheter. Therefore, the distal end portion of the conventional guide wire needs to have such a flexibility that the guide wire does not damage the wall of a blood vessel, adapts itself to the shape of a meandering blood vessel, and is insertable into a complex vascular branching.

However, as described above, since the distal end portion of the conventional guide wire is made of a general metallic material or plastics, plastic deformation is caused to the distal end portion when a certain value of displacement is exceeded, whereby the flexible movability of the guide wire for reaching a predetermined position in the blood vessel is endangered. Furthermore, even if the distal end portion of the guide wire reaches the predetermined position in the blood vessel, the distal end portion is lowered in its rebound due to plastic deformation. Hence, while the forward end portion of the catheter is being advanced, there is no resistance between the distal end portion of the guide wire and the wall of blood vessel, which is required for retaining the forward end portion of the guide wire against the flexure stress of the catheter, with the result that the distal end portion of the guide wire is drawn out of the predetermined position of the blood vessel. And, in many cases, the retention of the guide wire at the predetermined position ends in a failure and much time is wasted for the manual operation. There has been proposed a guide wire, the distal end portion of which is previously deformed into a J-shape so as to prevent the wall of blood vessel from being damaged and the distal end portion of the guide wire from engaging the wall of the blood vessel during its movement in the blood vessel. However, the distal end portion of the guide wire of the type described never fails to be deformed into a rectilinear shape while it passes through the introducing needle. Hence, thereafter, the distal end portion of the guide wire is not restored to a perfect J-shape, and, in many cases, such a disadvantage is presented that the initial function is not satisfactorily fulfilled.

Furthermore, it is preferable that the above-described guide-wire has the outer diameter substantially equal to the inner diameter of the catheter, so that the catheter thus guided can expand the wall of skin and the wall of blood vessel naturally and smoothly. As for the distal end portion of the guide wire, it is preferable that, to prevent the blood from leaking out through a gap formed between the introducing needle and the guide wire when the guide wire is inserted into the introducing needle, the distal end portion has the outer diameter substantially equal to the inner diameter of the introducing needle, i.e., the outer diameter of the body portion of the guide wire. Therefore, in the above-described guide wire, it is preferable that the outer diameter of the guide wire is made substantially equal to the inner diameter of the distal end portion of the catheter to guide the guide wire, whereby, even if the outer diameter of the guide wire is increased, both the body portion and the distal end portion can be provided with the elastic strain characteristics required, respectively.

One object of the present invention is to provide a guide wire for a catheter making the catheter reliably and readily introducible to a predetermined position.

More specifically, such object is to provide a guide wire capable of avoiding buckling when the body portion of the guide wire is inserted and covered by the manual operation.

Another object of the present invention is to provide a guide wire capable of being restored to the original state, even if the guide wire buckles, and not affecting the insertion and the covering.

A further object of the present invention is to provide a guide wire having the distal end portion flexible enough to be insertable, even when a complicated vascular system is encountered, and a good restoring force against deformation.

A still further object of the present invention is to provide a guide wire having the distal end portion, which constantly has a suitable rebound and may be retained at a predetermined position when it guides the catheter.

A yet further object of the present invention is to provide guide wires of various outer diameters, having the physical properties substantially identical with one another.

SUMMARY OF THE INVENTION

To the above end, the present invention contemplates that, in a guide wire for a catheter having the body portion comparatively high in rigidity and the distal end portion comparatively flexible, at least portions of the body portion and the distal end portion are formed of a super-elastic metallic member.

Further, the present invention contemplates that the body portion is formed of a super-elastic metallic member.

Also, the present invention contemplates that the distal end portion is formed of a super-elastic metallic member.

Moreover, the present invention contemplates that both the body portion and the distal end portion are formed of a super-elastic metallic member.

Furthermore, the present invention contemplates that at least a portion of the distal end portion is made smaller in cross-section than the body portion, and a portion between the body portion and the distal end portion is progressively reduced in cross-section from the body portion toward the distal end portion.

To the above end, the present invention contemplates that, in a guide wire for a catheter, wherein an inner core is constituted by an inner core portion on the body portion's side and an inner core portion on the distal end portion's side, the inner core as a whole is coated by a coating portion made of plastic and the guide wire includes the body portion comparatively high in rigidity and the distal end portion comparatively flexible, at least portions of the inner core portion on the body portion's side and the inner core portion on the distal end portion's side are formed of a super-elastic metallic member, and a portion of the inner core portion on the distal end portion's side is made smaller in cross-section than the inner core portion on the body portion's side.

Further, the present invention contemplates that at least a portion of the distal end portion including the aforesaid coating portion is made smaller in cross-section than the body portion.

Also, the present invention contemplates that the outer diameters of the coating portion at the distal end portion and the body portion are made equal to each other.

Moreover, the present invention contemplates that the inner core portion on the body portion's side is formed of a super-elastic metallic member.

Furthermore the present invention contemplates that the inner core portion on the distal end portion's side is formed of a super-elastic metallic member.

To the above end, the present invention contemplates that both the inner core portions on the body portion's side and on the distal end portion's side are formed of a super-elastic metallic member.

Further, the present invention contemplates that a portion between the body portion and the distal end portion is progressively reduced in cross-section from the body portion toward the distal end portion.

Also, the present invention contemplates that the coating portion is formed of a tube.

Moreover, the present invention contemplates that the coating portion is formed of a coating film.

BRIEF DESCRIPTION OF THE DRAWINGS

FIG. 1 is a plan view showing a first embodiment of the guide wire for a catheter according to the present invention;

FIG. 2 is a cross sectional view taken along the line II—II in FIG. 1;

FIG. 3 is a cross sectional view taken along the line III—III in FIG. 1;

FIG. 4 is a cross sectional view taken along the line IV—IV in FIG. 1;

FIGS. 5(A) through 5(D) are plan views showing modifications of the forms of the distal tip portion of the guide wire according to the present invention;

FIGS. 6(A) and 6(B) are plan views showing modifications of the forms of the distal end portion of the guide wire according to the present invention;

FIGS. 7 and 8 are graphic charts showing the flexure load-displacement value characteristics of the super-elastic metallic member and the general elastic metallic member;

FIG. 11 is a cross sectional view taken along the line XI—XI in FIG. 10;

FIG. 12 is a cross sectional view taken along the line XII—XII in FIG. 10;

FIG. 13 is a cross sectional view taken along the line XIII—XIII in FIG. 10;

FIGS. 14(A) and 14(B) are plan views showing modifications of the forms of the distal tip portion of the guide wire according to the present invention;

FIGS. 15(A) and 15(B) are plan views showing modifications of the distal end portion of the guide wire according to the present invention;

DETAILED DESCRIPTION

Figure 9:
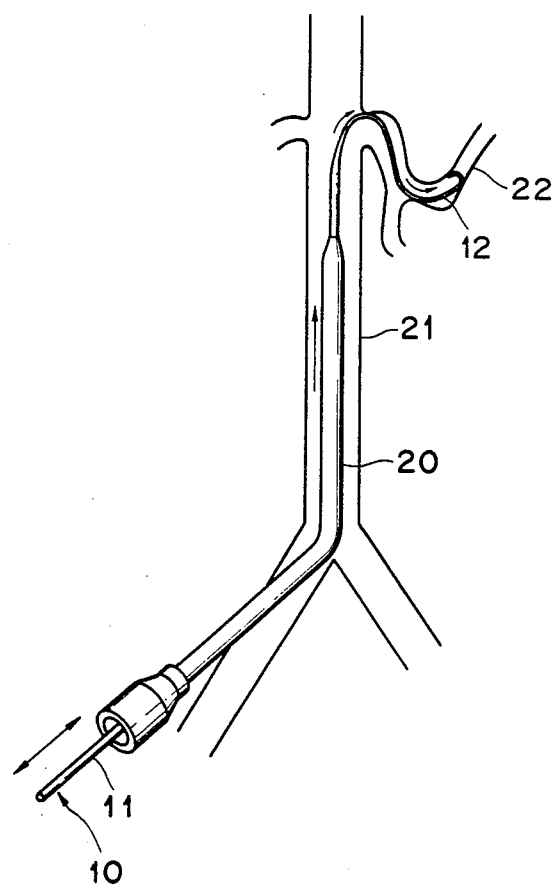
FIG. 9 is a schematic diagram showing the state of use of the guide wire according to the present invention.

FIG. 1 is a plan view showing the first embodiment of a guide wire 10 for a catheter according to the present invention. FIGS. 2 through 4 are cross sectional views taken along the lines II—II to IV—IV in FIG. 1.

The guide wire 10 has a body portion 11 comparatively high in rigidity and a distal end portion 12 comparatively flexible, and a tapered portion 13 disposed therebetween.

The aforesaid guide wire 10 is generally formed of a super-elastic (pseudo-elastic) metallic member such as a TiNi alloy of 49~58 atom % Ni, a Cu-Zn alloy of 38.5~41.5 wt % Zn, a Cu-Zn-X alloy of 1~10 wt % X (X=Be, Si, Sn, Al or Ga), an Ni-Al alloy of 36~38 atom % Al, or the like. The characteristic of super-elasticity is sometimes expressed as "pseudoelasticity".

In the body portion 11 of the guide wire 10, the outer diameter was determined to be 0.89 mm, the length 130 cm, and the yield stress then in a range between 10 and 80 Kg (Strograph M type produced by Toyo Seiki K. K.; the above-mentioned values were obtained under the conditions of a distance between the chucks being 80 mm, a speed of 5 mm/min and a tension temperature of 22° C.). The restoring stress (the yield stress under no load, indicated by B in FIG. 7) was determined to be 60 Kg/m m$^2$ (22° C.) or less. Additionally, the outer diameter of the body portion 11 may be in a range between 0.1 and 2 mm, and preferably be in a range between 0.45 and 1.15 mm. The length of the body portion 11 may be in a range between 10 and 300 cm. As for the distal end portion 12 of the guide wire 10, the outer diameter thereof is about 0.2 mm, the length about 20 cm, the yield stress in a range between 10 and 80 Kg/m m$^2$ and the restoring stress in a range between 0 and 60 Kg/m m$^2$ or less. Additionally, the outer diameter of the forward end portion 12 may be in a range between 0.05 and 1.5 mm, and preferably be in a range between 0.1 and 0.5 mm (provided it does not exceed the outer diameter of the body portion 11). Furthermore, the length of the distal end portion 12 in a range between 1 and 50 cm, preferably be in a range between 2 and 30 cm. The yield stress at the distal end portion in the embodiment was determined to be in a range between 18 and 24 Kg/m m$^2$ and the restoring stress in a range between 12 and 18 Kg/m m$^2$.

The distal tip portion 14 of the distal end portion 12 of the guide wire 10 is formed into an R-shape in order to prevent it from piercing the wall of a blood vessel (not shown). Furthermore, the tapered portion 13 is progressively reduced in cross-section from the body portion 11 toward the distal end portion 12, whereby the rigidity in a connecting portion between the body portion 11 and distal end portion 12 is moderately varied, so that breakage and bending of the guide wire 10 in this connecting portion can be prevented from occurring.

In order to prevent the distal tip portion of the distal end portion 12 of the guide wire 10 from piercing the wall of the blood vessel, the shape of the distal tip portion need not necessarily be limited to the R-shape, but, may be formed into a spherical shape designated by 15 in FIG. 5(A), a J-shape denoted by 16 in FIG. 5(B), a coil-shape indicated by 17 in FIG. 5(C), a ring-shape designated by 18 in FIG. 5(D) or the like.

As shown in FIGS. 6(A) and 6(B), the distal end portion 12A and 12B of the guide wire 10 are curvedly formed into predetermined shapes similar to the vascular system or vascular branching, so that the distal end portions can be reliably and readily inserted into predetermined position in the blood vessel.

The connecting portion between the body portion 11 and the distal end portion 12 of the guide wire 10 need not necessarily be formed into the tapered shape, but a cross-sectional shape may be adopted so that no considerable change in cross-section occurs between the body portion 11 and the distal end portion 12, or the connecting portion may have an outer diameter intermediate in size between the body portion 11 and the distal end portion 12.

FIG. 7 is a graphic chart in which the flexure load (W)-displacement value (D) characteristics of a TiNi alloy forming a cantilever beam of an outer diameter of 0.6 mm and a length of 20 mm is indicated by solid lines, and the flexure load-displacement value characteristics of a stainless steel wire forming a cantilever beam of an outer diameter of 0.45 mm and a length of 20 mm is indicated by broken lines. FIG. 8 is a graphic chart in which the flexure load-displacement value characteristics of a TiNi alloy forming a cantilever beam of an outer diameter of 0.1 mm and a length of 20 mm is indicated by solid lines, and the flexure load-displacement value characteristics of a stainless steel wire forming a cantilever beam is indicated by broken lines. In FIGS. 7 and 8, designated at E is a residual plastic strain value of the stainless steel wire. More specifically, according to FIGS. 7 and 8, the super-elastic metallic member (1) is high in restorable elastic strain to reach several % to ten-odd %, and (2) has the characteristics such that, even if the strain is increased, the load is not varied in value. In consequence, the body portion 11 of the guide wire 10 is formed of a super-elastic metallic member having a flexure load-displacement value characteristic substantially equal to that indicated by the solid lines in FIG. 7, whereby the body portion 11 is provided with the elastic strain characteristics having a comparatively high buckling strength. Furthermore, the distal end portion 12 of the guide wire 10 is formed of the super-elastic metallic member having the flexure load-displacement value characteristics substantially equal to that indicated by the solid lines in FIG. 8, whereby the distal end portion 12 is provided with elastic strain characteristics capable of being displaced to a comparatively high extent under a given stress and restorable.

Description will hereunder be given of operation of the first embodiment.

The guide wire 10 is of the rectilinear type in FIG. 1, or of various shapes desirably formed near the distal end portions of catheters 20 as shown in FIG. 9. A curved forward end portion, for example, of the catheter 20, the forward end portion of which is desirably formed into any one of various shapes, is inserted therethrough with the guide wire 10 being of a rectilinear shape shown in FIG. 1 of with the body portion 11 of the guide wire 10, which is comparatively high in rigidity to thereby be turned into a rectilinear shape, so that the catheter 20 can be smoothly advanced in a blood vessel 21 as shown in FIG. 9. Furthermore, the guide wire 10 causes the distal end portion 12 thereof to proceed ahead of the distal end portion of catheter 20, so that the distal end portion 12 can guide the distal end portion of the catheter to a predetermined position 22 in the blood vessel.

The body portion 11 of the guide wire 10 is provided with an elastic strain characteristic comparatively high in yield stress. In consequence, even if a comparatively high flexural deformation is caused to the body portion 11 when the guide wire 10 is inserted into the blood vessel, the guide wire 10 does not reach the plastic deformation region and is not subjected to buckling, so that the buckling limit of the body portion 11 can be improved. More specifically, even if a deformation of a high value is caused to the body portion 11 by the manual operation applied to the guide wire 10, a portion subjected to this deformation can be readily straightened again, so that no resistance is caused to the advance of the catheter. Furthermore, when the catheter provided at the distal end thereof with the curved portion is covered while being straightened, no resistance of a considerable value occurs between the catheter and the body portion 11, so that the catheter can smoothly advance.

Furthermore, the guide wire 10 is provided at the distal end portion 12 with elastic strain characteristics capable of being displaced to a comparatively high extent under a given stress and restorable. In consequence, while the distal end portion 12 goes through a bent portion of the blood vessel, a flexural deformation of a high value can be obtained under a load of a comparatively low value, and a curved deformation and its restoration are repeated. Thus the accommodation in shape of the guide wire 10 to the meandering blood vessel is improved and the guide wire 10 can be comparatively easily curved according to a vascular branching, so that the guide wire 10 can be smoothly advanced to a predetermined position in the blood vessel. Additionally, when the catheter is inserted to a predetermined position in the blood vessel, the guide wire 10 is provided at the distal end portion 12 with a rebound enough to generate a resistance against the wall of blood vessel, which is required for retaining the guide wire 10 at the predetermined position against the flexure stress of the catheter. As result, the distal end portion 12 is not drawn out of the predetermined position in the blood vessel and the catheter is suitably retained. Even if the distal end portion 12, which has been previously curvedly deformed, is straightened while passing through the introducing needle, the distal end portion 12 is restored to the perfect curved shape when inserted into the blood vessel thereafter, so that the original function can be fully satisfied.

The guide wire 10 has no irregularities on the surface thereof, differing from the conventional coil-shaped guide wire, whereby the guide wire 10 satisfactorily acts on the blood coagulation and the tensile strength is high as compared with the plastic guide wire, to thereby be safer than the latter.

The guide wire 10 is satisfactory in torque transmission performance in either one of torsional directions, differing from the conventional coil-shaped guide wire. A torque applied to the body portion 11 makes it possible to reliably and readily direct the distal end portion 12 toward a predetermined position in the blood vessel, so that controllability in inserting the distal end portion 12 to a position in a complicated vascular system can be improved.

In addition, in the above embodiment, description has been given of the guide wire 10, in which both the body portion 11 and the distal end portion 12 are formed of the super-elastic metallic member. However, according to the present invention, only the body portion of the guide wire may be formed of the super-elastic metallic member, and further, provided with an elastic strain characteristic having a yield stress of a comparatively high value. Or, only the distal end portion of the guide wire is formed of the super-elastic metallic member, and further, provided with an elastic strain characteristic capable of being displaced to a comparatively high extent under a given stress and restorable.

Figure 10:
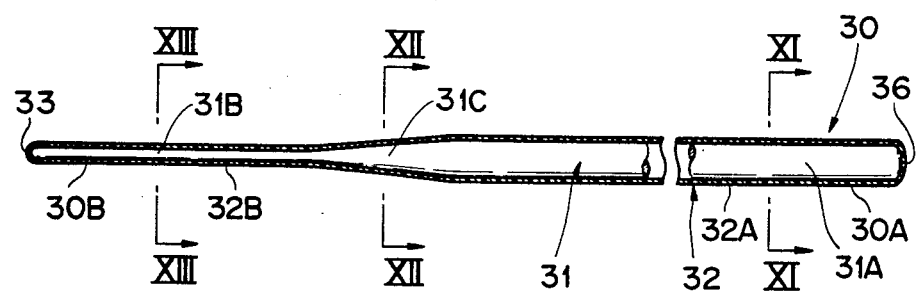
FIG. 10 is a plan view showing a second embodiment of the guide wire for a catheter according to the present invention.

FIG. 10 is a plan view showing the second embodiment of the guide wire 30 for a catheter according to the present invention. FIGS. 11 through 13 are cross sectional views taken along lines XI—XI through XIII—XIII in FIG. 10.

The guide wire 30 includes an inner core 31 and a coating portion 32, and is constituted by a body portion 30A and a distal end portion 30B.

The inner core 31 of the guide wire 30 is constituted by an inner core portion 31A on the body portion's side and an inner core portion 31B on the distal end potion's side, both of which are integrally formed through a tapered portion 31C. The inner core 31 is generally formed of a super-elastic (pseudo-elastic) metallic member such as a TiNi alloy of 49~58 atom % Ni, a Cu-Zn alloy of 38.5~41.5 wt %, a Cu-Zn-X alloy of 1~10 wt %X (X=Be, Si, Sn, Al or Ga), an Ni—Al alloy of 36~38 atom %Al, or the like.

The coating portion 32 of the guide wire 30 includes a coating portion 32A on the body portion's side and a coating portion 32B on the distal end portion's side. The coating portion 32 is made of elastomer or a composite material of synthetic resin materials including polyethylene, polyvinyl chloride, polyester, polypropylene polyamide, polyurethane, polystyrene, fluroine plastics and silicone rubber, or an elastomer or a composite material of the above-mentioned plastics, to thereby from a soft, smooth surface with no irregularities thereon. In addition, the coating portion 32 can obtain an anti-coagulating agent such as heparin and urokinase, or through coating of an anti-thrombus material such as silicone rubber, a block copolymer of urethane and silicone (®Avcothane), a copolymer of hydroxyethyl methacrylate-styrene and the like, and can obtain low friction properties by use of resin having a low frictional surface such as fluoro resin, and through applying a lubricant such as silicone oil. Furthermore, an X-ray contrast medium made of a single substance of metal such as Ba, W, Bi, Pb or the like, or a compound therebetween is mixed with a synthetic resin material forming the coating portion 32, so that the position of the guide wire 30 in the blood vessel can be accurately determined.

As for the body portion 30A of the guide wire 30, the outer diameter of the inner core potion 31A on the body portion's side is determined to be 0.62 mm, the outer diameter of the coating portion 32A on the body portion's side 0.89 mm, the length 130 cm, the yield stress in a range between 10 and 80 Kg/m m$^2$ (22° C.) (yield stress under load: A in FIG. 17), and the restoring stress (yield stress under no load: B in FIG. 17) in a range between 0 and 60 Kg/m m$^2$ (22° C.). In addition, the outer diameter of the inner core portion 31A on the body portion's side is in a range between 0.1 and 1.9 mm, and preferably in a range between 0.35 and 1.05 mm. The buckling strength is determined to be in a range between 10 and 80 Kg/m m$^2$ (22° C.), and the restoring stress in a range between 0 and 60 Kg/m m$^2$ (22° C.). Additionally, the outer diameter of the coating portion 32A on the body portion's side is determined to be in a range between 0.2 and 2 mm, and preferably in range between 0.45 and 1.15 mm. The length of the body portion 30A may preferably be in a range between 10 and 300 cm.

As for the distal end portion 30B of the guide wire 30, the outer diameter of the inner core portion 31B on the distal end portion's side is determined to be 0.2 mm, the outer diameter of the coating portion 32B on the distal end portion's side 0.47 mm, the length in a range between 0 and 150 mm, and preferably in a range between 2 and 150 mm, and more preferably be 20 mm, and the yield stress in a range between 10 and 80 Kg/m m² (22° C.). In addition, the outer diameter of the inner core portion 31B on the distal end portion's side is determined to be in a range between 0.05 and 1.5 mm, and preferably in a range between 0.1 and 0.5 mm, the flexure load in a range between 0.1 and 10 g, and the restoring load in a range between 0.1 and 10 g. Furthermore, the outer diameter of the inner core portion on the distal end portion's side as a whole need not necessarily be limited to the above-described dimensions, but, may partially adopt such dimensions. Further, the restoring stresses of the body portion and the distal end portion need not have the values equal to each other, but it is preferable that the restoring stresses may be varied in accordance with conditions of the heat treatment so as to obtain suitable properties by use of suitable diameters of the wire. In other words, it is preferable to separate the body portion and the distal end portion in heat treatment, so that the restoring stress in the body portion can be high in value and the distal end portion flexible. Then, the diameter of the wire of the inner core on the distal end portion's side is not made too small, so that the mechanical strength thereof can be improved. Furthermore, the outer diameter of the coating portion 32B is determined to in a range between 0.07 and 2 mm, and preferably be in a range between 0.12 and 1.10 mm. The outer diameter of the forward end portion including the coating portion as a whole need not necessarily be limited to the above-described dimension, but, may partially adopt such dimension. Furthermore, the length of the distal end portion 30B may preferably be determined to be in a range between 1 and 50 cm. The outer diameter of the coating portion may preferably be equal to that of the body portion.

Furthermore, in general, the coating portion 32 is closely fused to the inner core 31 through the above-described synthetic resin member, and a distal tip portion 33 and a rear end portion, i.e., a proximal end portion 36 are solidly secured to each other in the same manner as described above. However, when the coating portion 32 is formed of a hollow tube, in addition to the specific form of closely coating the guide wire 30 over the total length, it is preferable that the guide wire 30 is affixed to the inner core 31 through bonding or fusing at the distal tip portion 33 and the proximal end portion 36, or at a suitable position of the body portion of the guide wire 30. In this case, portions of the distal tip portion 33 and the proximal end portion 36 or a portion at a suitable position of the body portion, are not substantially over the total length bonded or fixed to the inner core 31. Thus, when flexed, the guide wire 30 is not restrained by the inner core 31, freely movable relative to the inner core 31, and particularly, flexibly deformable in the distal end portion 30B thereof. In addition, the coating portion according to the present invention may be constructed such that a coating film made of the above-described synthetic resin member is applied to the surface of the inner core 31. In this case also, it is preferable that the coating portion is not solidly secured to at least the inner core portion 31B on the distal end portion's side, so that the distal end portion 30B of the guide wire 30 may be flexibly deformed. The guide wire according to the present invention does not adopt a spring, whereby the form of fixing the coating portion to the inner core is not specified.

The distal tip portion 33 of the distal end portion 30B of the guide wire 30 is formed into an R-shape in order to prevent it from piercing the wall the blood vessel. Furthermore, the tapered portion 31C is progressively reduced in cross-section from the body portion 30A toward the distal end portion 30B, whereby the rigidity in a connecting portion between the body portion 30A and the forward end portion 30B is moderately varied, so that breakage and bending of the guide wire 30 in this connecting portion can be prevented from occurring.

In order to prevent the distal tip portion of the distal end portion 30B of the guide wire 30 from piercing the wall of the blood vessel, the shape of the distal tip portion need not necessarily be limited to the R-shape, but, may be formed into a spherical shape designated by 34 in FIG. 14(A) and a J-shape denoted by 35 in FIG. 14(B).

As shown in FIGS. 15(A) and 15(B), the distal end portion 30B of the guide wire 30 is curvedly formed into a predetermined shape similar to the vascular system or vascular branching, so that the distal end portion can be reliably and readily inserted into a predetermined portion in the blood vessel.

The distal end portion 30B of the guide wire 30 may be progressively reduced in diameter toward the distal tip portion 33, so that the distal end portion 30B can be made more flexible.

The connecting portion between the body portion 30A and the distal end portion 30B of the guide wire 30 need not necessarily be formed into the tapered shape, but, a cross-sectional shape may be adopted so that no considerable change in cross-section occurs between the body portion 30A and the distal end portion 30B, or the connecting portion may have an outer diameter intermediate in size between the body portion 30A and the distal end portion 30B.

This inner core need not necessarily be limited to the one formed by a single wire, but, a plurality of wires arranged in parallel to one another or twisted together may be used, so that the above-described function, i.e., a gradual or progressive change in the physical properties may be fulfilled.

Figure 16:
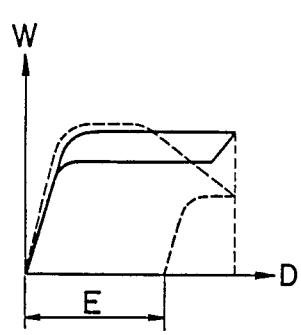
FIGS. 16 and 17 are graphic charts showing the flexure load-displacement value characteristics of the super-elastic metallic member and the general elastic metallic member.
Figure 17:
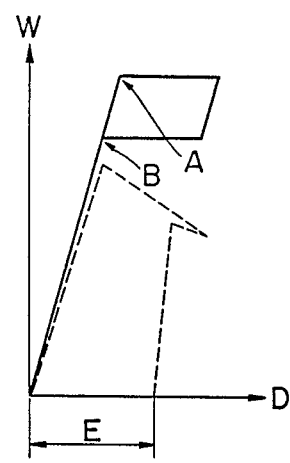

FIG. 16 is a graphic chart in which the flexure load (W)-displacement value (D) characteristics of a TiNi alloy forming a cantilever beam coated by a coating portion made of polyethylene of an outer diameter of 0.89, mm and having an outer diameter of 0.62 mm and a length of 20 mm is indicated by solid lines, and the flexure load-displacement value characteristics of a stainless steel wire forming a cantilever beam coated by a coating portion made of polyethylene of an outer diameter of 0.89, mm and having an outer diameter of 0.45 mm and a length of 20 mm is indicated by broken lines. FIG. 17 is a graphic chart in which the flexure load-displacement value characteristics of a TiNi alloy forming a cantilever beam coated by a coating portion made of polyethylene of an outer diameter of 0.42, mm and having an outer diameter of 0.15 mm and a length of 20 mm is indicated by solid lines, and the flexure load-displacement value characteristics of a stainless steel wire forming a cantilever beam coated by a coating portion made of polyethylene of an outer diameter of 0.42, mm and having an outer diameter of 0.10 mm and a length of 20 mm is indicated by broken lines. In FIGS. 16 and 17, designated at E is a residual plastic strain value of the stainless steel wire. More specifically, according to FIGS. 16 and 17, the super-elastic metallic member (1) is high in restorable elastic strain, and (2) has the characteristics that, even if the strain is increased, the load is not varied in value. In consequence, the body portion 30A of the guide wire 30 is formed of the inner core portion 31A made of a super-elastic metallic member having the flexure load-displacement value characteristics substantially similar to that indicated by the solid lines in FIG. 16 and the coating portion 32A made of the synthetic resin material, whereby the body portion 30A is provided with elastic strain characteristics having a comparatively high buckling strength. Furthermore, the distal end portion 30B of the guide wire 30 is formed of the inner core portion 31B made of the super-elastic metallic member having flexure load-displacement value characteristics substantially equal to that indicated by the solid lines in FIG. 17 and the coating portion 32B made of the synthetic resin material, whereby the distal end portion 30B is provided with an elastic strain characteristic capable of being displaced to a comparatively high extent under a given stress and restorable.

Figure 18:
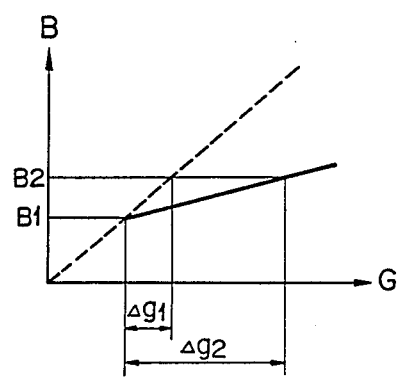
FIG. 18 is a graphic chart showing the flexural rigidity-maximum outer diameter characteristics of the guide wire.

FIG. 18 is a graphic chart in which the flexural rigidity(B)-maximum outer diameter (G) characteristics of the guide wire, the inner core portion of which is formed of the super-elastic metallic member and coated by the coating portion made of plastic, is indicated by solid lines, and the flexural rigidity-maximum outer diameter characteristics of a guide wire formed of only the super-elastic metallic member is indicated by broken lines. According to this FIG. 18, in the guide wire formed of only the super-elastic metallic member, the range of the maximum outer diameter (Δgl) satisfying the determined flexure rigidity(B1∼B2) is small. In contrast, when the inner core 31 is coated by the coating portion 32 as in the aforesaid guide wire 30, the range of the maximum outer diameter (Δg2) satisfying the determined flexural rigidity is enlarged to a great extent, and it is recognized that, when the inner diameter of the catheter to be guided becomes large, the body portion 30A may be formed to have an outer diameter substantially equal to the inner diameter of the catheter, with the flexural rigidity being held within a predetermined range.

Description will hereunder be given of operation of the second embodiment.

Figure 19:
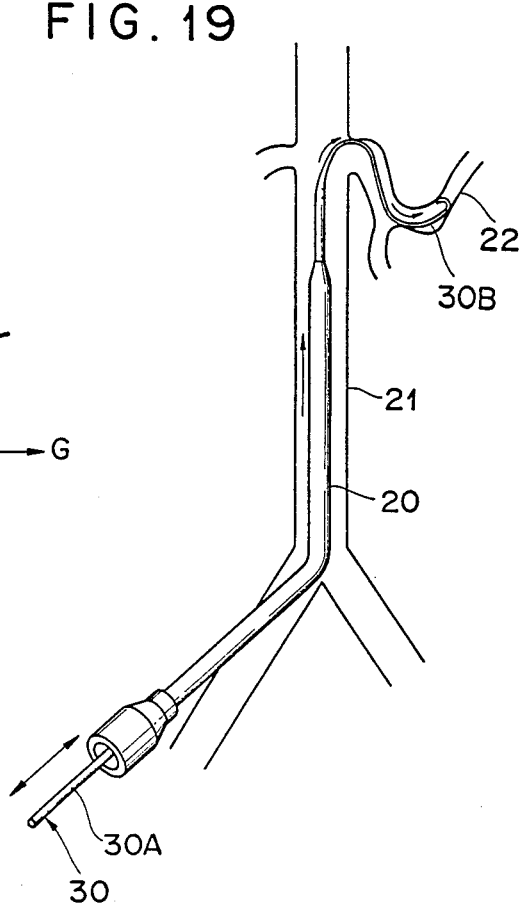
FIG. 19 is a schematic diagram showing the state of use of the guide wire according to the present invention.

The guide wire 30 is of various shapes desirably formed near the distal end portions of the catheters 20 as shown in FIG. 19. A curved portion thereof, for example, is straightened and inserted into the body portion 30A comparatively high in rigidity, so that the catheter 20 can be smoothly advanced in the blood vessel 21. Furthermore, the guide wire 30 causes the distal end portion 30B thereof to proceed ahead of the distal end portion of the catheter 20, so that the distal end portion 30B can guide the distal end portion of the catheter to a predetermined position 22 in the blood vessel.

Here, since the inner core 31 of the guide wire 30 is coated by the coating portion 32, the diameter of the inner core 31 may be made small even when the catheter to be guided is large in its diameter, and there may be obtained an outer diameter of the inner core 31 corresponding to the inner diameter of the catheter to be guided, with the flexural rigidity being held within a predetermined range, so that the catheter can naturally and smoothly dilate the skin and the wall of the blood vessel.

In the guide wire 30, the inner core portion 31B on the distal end portion's side and the coating portion 32B on the distal end portion's side are made smaller in cross-section than the inner core portion 31A on the body portion's side and the coating portion 32A on the body portion's side, respectively, whereby the distal end portion 30B is made smaller in cross-section than the body portion 30A. Accordingly the body portion 30A may be provided with elastic strain characteristics having a comparatively high buckling strength and the distal end portion 30B may be provided with the elastic strain characteristics capable of being displaced to a comparatively large extent under a given stress and restorable.

More specifically, the body portion 30A of the guide wire 30 is provided with the elastic strain characteristics having a comparatively high bucking strength. In consequence, even if a flexural deformation of a comparatively high value is caused to the body portion 30A when the guide wire is inserted into the catheter and the blood vessel, the guide wire 30 does not reach the plastic deformation region and is not subjected to buckling, so that the buckling limit of the body portion 30A can be improved. More specifically even if a deformation of a high value is caused to the body portion 30A by the manual operation applied to the guide wire 30, a portion subjected to this deformation can be readily straightened again, so that no resistance is caused to the advance of the catheter. Furthermore, when the catheter provided at the distal end thereof with the curved portion is crownedly coupled while being straightened, no resistance of a considerable value occurs between the catheter and the body portion 30A, so that the catheter can smoothly advance.

Furthermore, the guide wire 30 is provided at the distal end portion 30B thereof with an elastic strain characteristic capable of being displaced to a comparatively high extent under a given stress and restorable. In consequence, while the distal end portion 30B goes through a bent portion of the blood vessel, a flexural deformation of a high value can be obtained under a load of a comparatively low value, a curved deformation and its restoration are repeated, whereby the accommodiation in shape of the guide wire 30 to the meandering blood vessel is improved and the guide wire 30 can be comparatively easily curved according to a given vascular branching. As a result the guide wire 30 can be smoothly advanced to a predetermined position in the blood vessel. Additionally, when the catheter is inserted to a predetermined position in the blood vessel, the guide wire 30 is provided at the distal end portion 30B thereof with a rebound enough to generate a resistance against the wall of blood vessel, which is required for retaining the guide wire 30 at the predetermined position against the flexure stress of the catheter. As the result, the distal end portion 30B is not drawn out of the predetermined position in the blood vessel and the catheter is suitably retained. Even if the distal end portion 30B, which has been previously curvedly deformed, is straightened while passing through the introducing needle, the distal end portion 30B is restored to the perfect curved shape when inserted into the blood vessel thereafter, so that the original function can be fully satisfied. The guide wire 30 has no irregularities on the surface thereof, differing from the conventional coil-shaped guide wire, whereby the guide wire 30 satisfactorily acts on the blood coagulation and the tensile strength is high as compared with the plastic guide wire, to thereby be safer than the latter.

The guide wire 30 is satisfactory in torque transmission performance in either one of the torsional directions, differing from the conventional coil-shaped guide wire. A torque applied to the body portion 30A makes it possible to reliably and readily direct the distal end portion 30B toward a predetermined position in the blood vessel, so that controllability in inserting the distal end portion 30B to a position in a complicated vascular system can be improved.

In addition, in the above embodiment, description has been given of the guide wire 30, in which both the body portion 30A and the distal end portion 30B are formed of the super-elastic metallic member. However, according to the present invention, only the body portion of the guide wire may be formed of the super-elastic metallic member, and further, provided with elastic strain characteristics having a buckling strength of a comparatively high value. Or, only the distal end portion of the guide wire is formed of the super-elastic metallic member, and further, provided with elastic strain characteristics capable of being displaced to a comparatively high extent under a given stress and restorable.

As described above, according to the present invention, in guide wire for a catheter, having a body portion comparatively high in rigidity and a distal end portion comparatively flexible, at least portions of the body portion and the distal end portion are formed of a super-elastic metallic member. In consequence, the catheter can be reliably and readily introduced to a predetermined position.

Figure 20:
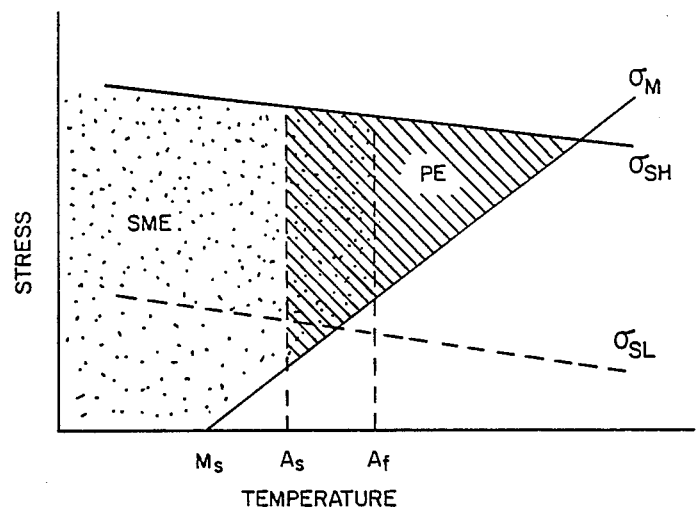
FIG. 20 is a graph showing conditions under which certain effects appear in the guide wire of the present invention.

FIG. 20 is a graph showing conditions under which shape memory effect (SME) and pseudo-elasticity (PE) appear. In the graph, $\sigma M$ is the critical stress extending to the stress inducing transformation $\sigma SH$, and $\sigma SL$ is the critical stress for permanent deformation such as slip.

In order to allow an alloy to "remember" a shape, the alloy should be formed into the desired shape while in a certain temperature region (As-Af) as shown in FIG. 20. Accordingly, when the alloy is formed into a provisional shape while below a certain temperature Ms, the desired shape is hidden. If the temperature is gradually increased and exceeds the temperature As, then the desired shape appears again. If the temperature exceeds Af, than the memory disappears and, hence, the alloy must be worked on again to establish the desired shape memory in the temperature region (As-Af).

The values of Ms, As, Af and (As-Af) are characteristic ones determined by the respective compositions. For example, for an alloy of (Ti-Ni of 55-56 atom % Ni, C of less than 0.07 w %), Ms is $-45°$ C., As is $-15°$ C. and Af is $-5°$ C.

SME and PE are entirely different in characteristics from one another.

SME is utilized when changes in temperature in the working environment are utilized to present shapes suitable to the respective conditions. For example, SME may be used to that an object is in straight form for easy insertion at room temperature, and attains a shape similar to a blood vessel in which the alloy remains when elevated to the blood temperature.

PE is utilized, in the present invention, to obtain outstanding pseudo-elasticity wherein the alloy can be easily flexed by a small stress applied when in contact with the wall of a blood vessel and easily restored. That is, the present guide wire is easily inserted into a blood vessel and avoids serious damage to the wall of the blood vessel owing to the effective utilization of the PE characteristic.

It will be appreciated that both SME and PE are not present in an alloy at the same temperature. Thus, should the SME effect prevail in a temperature range corresponding to that of a patient's blood, the alloy would not posses sufficient PE to allow it to be used as a guide wire for insertion into deep portions of blood vessels, particularly in a non-coiled mono-filament form.

It is preferred that the temperature at which transformation to austenite is complete be restricted to 10° C. or less. The reason is that for the guide wire to be usable in the human body it must operate in the range of about 10°-20° C. due to anaesthesia at a low body temperature.

In summary according to the present invention, the body portion is formed of the super-elastic metallic member, so that the body portion can be provided with the elastic strain characteristics having a yield stress comparatively high in value.

Further, the distal end portion is formed of the super-elastic metallic member, so that the distal end portion can be provided with the elastic strain characteristics capable of being displaced to a comparatively high extent under a given stress and restorable.

Also, both the body portion and the distal end portion are formed of the super-elastic metallic member, so that the body portion can be provided with the elastic strain characteristics having a comparatively high yield stress and the distal end portion can be provided with the elastic strain characteristics capable of being displaced to a comparatively high extent under a given stress and restorable.

Moreover, the distal end portion is made smaller in cross-section than the body portion, and a portion between the body portion and at least a portion of the distal end portion is progressively reduced in cross-section from the body portion toward the distal end portion, whereby a change in rigidity in a connecting portion between the body portion and the distal end portion is made moderate, so that breakage and bending of the guide wire in the connecting portion can be prevented from occurring.

Furthermore, according to the present invention, in a guide wire for the catheter, wherein the inner core is constituted by an inner core portion on the body portion's side and an inner core portion on the distal end portion's side, the inner core as a whole is coated by a coating portion made of plastic, and the guide wire has the body portion comparatively high in rigidity and the distal end portion comparatively flexible, at least a portion of the inner core portion on the body portion's side and the inner core portion on the distal end portion's side are formed of the super-elastic metallic member, and at least a portion of the inner core portion on the distal end portion's side is made smaller in cross-section than the inner core portion on the body portion's side. In consequence, the catheter can be reliably and readily introduced to a predetermined position.

Further, the outer diameter of at least a portion of the distal end portion including the coating portion is made smaller in cross-section than that of the body portion, so that the catheter can be reliably and readily introduced to a predetermined position.

Also, the outer diameters of the coating portion at the distal end portion and the body portion are made equal to each other, so that blood can be prevented from leaking out when an introducing needle is inserted, and the catheter can naturally and smoothly expand the wall of skin and the wall of blood vessel.

Moreover, the inner core portion on the body portion's side is formed of the super-elastic metallic member, so that the body portion can be provided with the elastic strain characteristics having the buckling strength comparatively high in value.

Furthermore to the present invention, the inner core portion on the distal end portion's side is formed of the super-elastic metallic member, so that the distal end portion can be provided with the elastic strain characteristics capable of being displaced to a comparatively high extent under a given stress and restorable.

Further, both the inner core portion on the body portion's side and the inner core portion on the distal end portion's side are formed of the super-elastic metallic member, so that the body portion can be provided with the elastic strain characteristics having the buckling strength comparatively high in value, and the distal end portion can be provided with the elastic strain characteristics capable of being displaced to a comparatively high extent under a given stress and restorable.

Also, at least a portion between the inner core portion on the body portion's side and the inner core portion on the distal end portion's side is progressively reduced in cross-section from the body portion toward the distal end portion, whereby rigidity in a connecting portion between the body portion and the distal end portion is varied moderately, so that breakage and bending of the guide wire in the connecting portion can be prevented from occurring.

Moreover, the coated portion is formed into a hollow pipe, so that the distal end portion can secure a high flexibility.

In addition, the coating portion may be formed of a coating film, so that the coating portion can be readily formed on the outer surface of the inner core.

What is claimed is:

1. A guide wire for inserting a surrounding tubular catheter into the body of a warm-blooded animal such as a human being, comprising:
   an elongate body portion comparatively high in rigidity and a comparatively flexible elongate distal end portion coupled axially to said body portion, wherein at least a portion of said distal end portion is smaller in cross-section than said body portion, and a portion between said body portion and said distal end portion is progressively reduced in cross-section from said body portion toward distal end portion and said distal end portion is substantially more flexible than said body portion, and
   at least a portion of at least one of said body portion and said distal end portion being formed of a super-elastic metallic member having a solid cross-section and being in a non-coiled monofilament form,
   said super-elastic metallic member including an alloy having a temperature at which transformation to austenite is complete which is at most about 10° C. so that said metallic member exhibits pseudoelasticity when inserted into the body of said warm-blooded animal,
   said alloy being selected from the group consisting of Ti-Ni alloy consisting essentially of 49-58 atom % Ni and the balance substantially Ti, Cu-Zn alloy consisting essentially of 38.5-41.5 wt. % Zn and the balance substantially Cu, Cu-Zn-alloy consisting essentially of 38.5-41.5 wt. % Zn, 1-10 wt. % X wherein X is Be, Si, Xn, Al or Ga, and the balance substantially Cu, and Ni-Al alloy consisting essentially of 36-38 atom % Al, and the balance substantially Ni.

2. The guide wire for a catheter as set forth in claim 1, wherein said body portion is formed of the super-elastic metallic member.

3. The guide wire for a catheter as set forth in claim 1, wherein said distal end portion is formed of the super-elastic metallic member.

4. The guide wire for a catheter as set forth in claim 1, wherein both the body portion and the distal end portion are formed of the super-elastic metallic member.

5. A guide wire for inserting a surrounding tubular catheter into the body of a warm-blooded animal such as a human being, comprising;
   an elongate body portion and an elongate distal end portion;
   coupled axially to said body portion; said body and distal end portions including:
   an inner core which includes a first inner core portion on said body portion's side and a second inner core portion on said distal end portion's side; an intermediate inner core portion between the inner core portion on the body portion's side and the inner core portion on the distal end portion's side, said intermediate inner core portion being progressively reduced in cross-section from the body portion toward the distal end portion; and
   whereby at least a portion of said distal end portion is smaller in cross-section than said body portion and
   a plastic coating covering said inner core as a whole; said body portion being comparatively high in rigidity and said distal and portion being substantially more flexible than said body portion;
   at least a portion of at least one of said first and second inner core portions being formed of a super-elastic metallic member having a solid cross-section and which includes an alloy selected from the group consisting of Ti-Ni alloy consisting essentially of 49-58 atom % Ni and the balance substantially Ti, Cu-Zn alloy consisting essentially of 38.5-41.5 wt % Zn and the balance substantially Cu, Cu-Zn-X, consisting essentially of 38.5-41.5 wt. % Zn, 1-10 wt, % X (X=Be, Si, Al or Ga) and the balance substantially Cu, and Ni-Al alloy consisting essentially of 36-38 atom % Al and the balance substantially Ni;
   the selected alloy forming said super-elastic metallic member being such that the temperature at which transformation to austenite is complete is at most about 10° C.; and
   at least a portion of said second inner core portion on the distal end portion's side being smaller in cross-section than said first inner core portion on the body portion's side,
   wherein the guide wire is in a non-coiled monofilament form, and said metallic member exhibits pseudo-elasticity when inserted into the body of said warm-blooded animal.

6. The guide wire for a catheter as set forth in claim 5, wherein said plastic coating has substantially equal outer diameters at the distal end portion and at the body portion.

7. The guide wire for a catheter as set forth in any one of claims 5 or 6, wherein said inner core portion on the body portion's side is formed of the super-elastic metallic member.

8. The guide wire for a catheter as set forth in any one of claims 5 or 6, wherein said inner core portion on the distal end portion's side is formed of the super-elastic metallic member.

9. The guide wire for a catheter as set forth in any one of claims 5 or 6, wherein both the inner core portions on the body portion's side and on the distal end portion's side are formed of the super-elastic metallic member.

10. The guide wire for a catheter as set forth in any one of claims 5 or 6, wherein said plastic coating comprises a hollow pipe.

11. The guide wire for a catheter as set forth in any one of claims 5 or 6, wherein said plastic coating comprises a coating film.

12. A guide wire for inserting a surrounding tubular catheter into the body of a warm-blooded animal such as a human being, comprising;
  an elongate body portion and an elongate distal end portion;
  coupled axially to said body portion; said body and distal end portions including:
  an inner core which includes a first inner core portion on said body portion's side and a second inner core portion on said distal end portion's side; and
  a plastic coating covering said inner core as a whole; said body portion being comparatively high in rigidity and having a yield stress in the range of 10 to 80 kg/mm$^2$ and said distal and portion being substantially more flexible than said body portion and having a yield stress less than the yield stress of said body portion and in the range of 10 to 80 kg/mm$^2$;
  at least a portion of at least one of said first and second inner core portions being formed of a super-elastic metallic member having a solid cross-section and which includes an alloy selected from the group consisting of Ti-Ni alloy consisting essentially of 49-58 atom % Ni and the balance substantially Ti, Cu-Zn alloy consisting essentially of 38.5-41.5 wt % Zn and the balance substantially Cu, Cu-Zn-X, consisting essentially of 38.5-41.5 wt. % Zn, 1-10 wt, % X (X=Be, Si, Al or Ga) and the balance substantially Cu, and Ni-Al alloy consisting essentially of 36-38 atom % Al and the balance substantially Ni;
  the selected alloy forming said super-elastic metallic member being such that the temperature at which transformation to austenite is complete is at most about 10° C.;
  at least a portion of said second inner core portion on the distal end portion's side being smaller in cross-section than said first inner core portion on the body portion's side,
  at least a portion of said distal end portion being smaller in cross-section than said body portion, and
  an intermediate inner core portion between the inner core portion on the body portion's side and the inner core portion on the distal end portion's side, said intermediate inner core portion being progressively reduced in cross-section from the body portion toward the distal end portion,
  wherein the guide wire is in a non-coiled monofilament form, and said metallic member exhibits pseudo-elasticity when inserted into the body of said warm-blooded animal.

* * * * *